United States Patent
Wang (10) Patent No.: US 9,321,822 B2
(45) Date of Patent: Apr. 26, 2016

(54) MILK FAT GLOBULE EPIDERMAL GROWTH FACTOR—FACTOR VIII AND SEPSIS

(75) Inventor: Ping Wang, Roslyn, NY (US)

(73) Assignee: The Feinstein Institute for Medical Research, Manhasset, NY (US)

(*) Notice: Subject to any disclaimer, the term of this patent is extended or adjusted under 35 U.S.C. 154(b) by 615 days.

(21) Appl. No.: 11/920,304

(22) PCT Filed: May 12, 2006

(86) PCT No.: PCT/US2006/018774
§ 371 (c)(1),
(2), (4) Date: Mar. 3, 2009

(87) PCT Pub. No.: WO2006/122327
PCT Pub. Date: Nov. 16, 2006

(65) Prior Publication Data
US 2009/0297498 A1  Dec. 3, 2009

Related U.S. Application Data (60) Provisional application No. 60/680,628, filed on May 13, 2005.

(51) Int. Cl.
*C07K 14/435* (2006.01)
*A61K 38/18* (2006.01)
*C07K 14/705* (2006.01)
*A61K 38/00* (2006.01)

(52) U.S. Cl.
CPC ............... *C07K 14/705* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,354,897 B2 * | 4/2008 | Gilbert et al. | 514/14.1 |
| 2004/0197314 A1 | 10/2004 | Delcayre et al. | |
| 2011/0105399 A1 | 5/2011 | Wang | |
| 2014/0121163 A1 | 5/2014 | Wang | |

FOREIGN PATENT DOCUMENTS

| | | | | |
|---|---|---|---|---|
| EP | 1 004 664 A1 | 5/2000 | | |
| EP | 1 459 756 A1 | 9/2004 | | |
| WO | WO/03/016522 | * 2/2003 | | C12N 15/00 |
| WO | WO/03/103700 | * 12/2003 | | A61K 38/16 |
| WO | WO 03/103700 A1 | 12/2003 | | |

OTHER PUBLICATIONS

Swiss-Prot entry Q08431.2—sequence updated Nov. 1, 1997.*
Zhou et al., Adrenomedullin and Adrenomedullin Binding Protein-1 Attenuate Vascular Endothelial Cell Apoptosis in Sepsis, Ann. Surgery, 240, 321-330, 2004.*
Hanayama et al. Identification of a factor that links apoptotic cells to phagocytes, Nature, 417, 182-187, 2002.*
NCBI entry for P21956, accessed Apr. 4, 2011.*
Kvistgaard et al., Inhibitory Effects of Human and Bovine Milk Constituents on Rotavirus Infections, J. Dairy Res. 87, 4088-4096, 2004.*
The Supplementary European Search Report for European Application No. EP 06 78 4414.
Miksa et al. "Dendritic cell-derived exosomes containing milk fat globule epidermal growth factor—factor VIII attenuate proinflammatory response in sepsis." Shock, vol. 25, No. 6, pp. 586-593, 2006.
The International Search Report and the Written Opinion of the International Searching Authority of PCT Application No. PCT/US2006/018774.
Zhou, et al., "Adrenomedullin and Adrenomedullin Binding Protein-1 Attenuate Vascular Endothelial Cell Apoptosis in Sepsis." Annals of Surgery 240:2, Aug. 2004, pp. 231-330.
Lee, et al., Milk Fat Globule-EGF Factor 8 Protein; Lactadherin; medin; O-acetyl Disialoganglioside Synthase [*Homo Sapiens*]. GenBank Accession No. NP-005919, Jan. 23, 2004.
The International Preliminary Report on Patentability for PCT Application No. PCT/US2006/018774, dated Nov. 22, 2007.
European Office Action dated Aug. 13, 2009, issued in corresponding European Application No. 06 784 414.2.
Australian Office Action dated Dec. 21, 2010, issued in corresponding Australian Application No. 2006243905.
Chinese Office Action dated Jun. 7, 2011, issued in corresponding Chinese Application No. 200680022383.6, in Chinese language and English language Translation thereof.

* cited by examiner

*Primary Examiner* — Elly-Gerald Stoica
(74) *Attorney, Agent, or Firm* — Amster, Rothstein & Ebenstein LLP (57) ABSTRACT

Provided are methods of treating a mammal undergoing sepsis or at risk for sepsis. Also provided are methods of preventing or treating a physiologic effect of sepsis in a mammal. Additionally provided is the use of milk fat globule epidermal growth factor-factor VIII (MFG-E8) for the manufacture of a medicament for preventing or treating a physiologic effect of sepsis in a mammal, and the use of milk fat globule epidermal growth factor-factor VIII (MFG-E8) for the treatment of a mammal having sepsis or at risk for sepsis.

5 Claims, 10 Drawing Sheets

FIG. 10 ized at $10-25 billion annually in the United

MILK FAT GLOBULE EPIDERMAL GROWTH FACTOR—FACTOR VIII AND SEPSIS

CROSS-REFERENCE TO RELATED APPLICATION

This is a U.S. national phase of PCT Application No. PCT/US2006/018774, filed May 12, 2006 and claims priority to U.S. Provisional Application No. 60/680,628, filed May 13, 2005.

STATEMENT OF GOVERNMENT SUPPORT

This invention was made with government support under grant GM057468 awarded by the National Institutes of Health. The government has certain rights in the invention.

BACKGROUND OF THE INVENTION (1) Field of the Invention

The present invention generally relates to treatment of sepsis. More specifically, the invention is directed to the use of milk fat globule epidermal growth factor-factor VIII (MFG-E8) to treat sepsis.

(2) Description of the Related Art

Despite advances in the management of trauma victims, the incidence of sepsis and septic shock has increased significantly over the past two decades. It has been estimated that in the United States alone, more than 750,000 patients develop sepsis and septic shock each year with an overall mortality rate of 28.6%. Severe sepsis is a common, expensive, and frequently fatal condition, with as many deaths annually as those from acute myocardial infarction. Sepsis is the 3rd leading cause of death overall in the United States. A recent report indicates that the average costs per septic patient are at least $22,100, with annual total costs of more than $16 billion nationally. Activated protein C (APC) is the only FDA-approved specific treatment for sepsis, but its use is limited to non-surgical adult patients with severe sepsis. APC cannot be used in trauma victims and surgical patients who develop sepsis, due to its adverse effects on coagulation. Thus, there is a great need for an effective novel therapy for sepsis, especially surgical sepsis. The market potential for sepsis treatment is estimated at $10-25 billion annually in the United States alone.

The present invention further addresses the role of MFG-E8 in sepsis and inflammation.

SUMMARY OF THE INVENTION

Accordingly, the inventor has discovered that treating a mammal with milk fat globule epidermal growth factor-factor VIII (MFG-E8) can prevent or reduce physiologic effects of sepsis, including inflammation.

Thus, in some embodiments, the invention is directed to methods of treating a mammal undergoing sepsis. The methods comprise treating the mammal with a milk fat globule epidermal growth factor-factor VIII (MFG-E8) such that a physiologic effect of the sepsis is prevented or reduced.

In other embodiments, the invention is directed to methods of treating a mammal at risk for sepsis. The methods comprise treating the mammal with a milk fat globule epidermal growth factor-factor VIII (MFG-E8) sufficient to prevent or reduce a physiologic effect of the sepsis.

Additionally, the present invention is directed to methods of preventing or treating a physiologic effect of sepsis in a mammal. The methods comprise treating the mammal with a milk fat globule epidermal growth factor-factor VIII (MFG-E8) such that a physiologic effect of the sepsis is prevented or reduced.

In additional embodiments, the invention is directed to the use of milk fat globule epidermal growth factor-factor VIII (MFG-E8) for the manufacture of a medicament for preventing or treating a physiologic effect of sepsis in a mammal.

The invention is also directed to the use of milk fat globule epidermal growth factor-factor VIII (MFG-E8) for the treatment of a mammal having sepsis or at risk for sepsis.

DETAILED DESCRIPTION OF THE INVENTION

The present invention is based in part on the discovery that treating a mammal with a milk fat globule epidermal growth factor-factor VIII (MFG-E8) can prevent or reduce physiologic effects of sepsis and inflammation.

Thus, in some embodiments, the present invention is directed to methods of treating a mammal undergoing sepsis. The methods comprise treating the mammal with a milk fat globule epidermal growth factor-factor VIII (MFG-E8) such that a physiologic effect of the sepsis is prevented or reduced. Preferably, the MFG-E8 has an amino acid sequence at least 80%, more preferably at least 90%, even more preferably 95%, still more preferably, at least 99% identical to SEQ ID NO:1 or SEQ ID NO:2, which are the sequences of a human MFG-E8 and mouse MFG-E8, respectively. Most preferably, the MFG-E8 sequence is completely homologous to SEQ ID NO: 1. These methods can be used with any mammal, including humans.

The MFG-E8 in these embodiments can be in purified form, e.g., as a protein purified from a natural source or as a transgenic protein expressed from a recombinant cell. Alternatively, the MFG-E8 can be in combination with other therapeutic agents and/or only partially purified (e.g., further comprising cellular components, such as in the form of MFG-E8-rich exosomes derived from bone marrow dendritic cells [see Examples] or from other mammalian cells, including cells transformed with transgenic MFG-E8). Where the MFG-E8 is from MFG-E8-rich exosomes, the exosomes are preferably from the same species as the treated mammal; more preferably, the exosomes are from the same individual. The MFG-E8 can have a wild-type sequence from any mammalian species, or can comprise mutations, provided the mutations do not eliminate the protein's activity to prevent or reduce a physiologic effect of the sepsis. Such mutants could be made without undue experimentation. The activity of those mutants can also be easily determined by known methods and the methods described herein.

The MFG-E8 can also comprise peptidomimetics. As used herein, an amino acid mimetic or peptidomimetic is a compound that is capable of mimicking a natural parent amino acid in a protein, in that the substitution of an amino acid with the peptidomimetic does not significantly affect the activities of interest of the protein, in this case, the therapeutic activity of exogenous MFG-E8 in phagocytosis, sepsis and inflammation. Proteins comprising peptidomimetics are generally poor substrates of proteases and are likely to be active in vivo for a longer period of time as compared to the natural proteins. In addition, they could be less antigenic and show an overall higher bioavailability. The skilled artisan would understand that design and synthesis of aqueous-soluble proteins comprising peptidomimetics would not require undue experimentation. See, e.g., Ripka et al. (1998) Curr. Opin. Chem. Biol. 2, 441-452; Kieber-Emmons et al. (1997) Curr. Opin. Biotechnol. 8, 435-441; Sanderson (1999) Med. Res. Rev. 19, 179-197.

The above-described MFG-E8 preparations are preferably formulated in a pharmaceutical composition. These compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The methods of the present invention prevent or reduce any physiologic effect of sepsis, including shock (which in turn affects endothelial cell function, smooth muscle contractility, cardiac output, stroke volume, systemic oxygen delivery, lactic acidosis, hemoconcentration, total peripheral vascular resistance and/or regional blood perfusion), renal function, hepatic function, gut absorptive function, adrenal function, insulin responsiveness, altered cytokine (e.g., IL-10, TNF-α, IL-1β and/or IL-6) release, and physiological effects of altered cytokine release (e.g., inflammation). To evaluate the prevention or reduction of physiologic effects of sepsis, it is preferred that physiologic effects that are easily measured are evaluated. Examples of these effects are elevation of serum TNF-α levels, elevation of serum ALT levels, elevation of serum AST levels, elevation of serum lactate, and elevation of serum creatinine. In preferred embodiments, the measured physiological effect of the sepsis is elevation of serum TNF-α or IL-6 levels, or evaluation of thymocyte apoptosis, as in the Example. Determination of shock, or its direct effects (e.g., hemoconcentration, peripheral vascular resistance, etc.) is also easily measured and can be utilized.

These methods can also comprise treating the mammal with a second treatment that can reduce a physiological effect of the sepsis. Nonlimiting examples of such treatments include administration of adrenomedullin, adrenomedullin binding protein, activated protein C, or an $\alpha_{2A}$-adrenergic antagonist. The latter treatment is described in U.S. Provisional Patent Application 60/680,999, entitled TREATMENT OF SEPSIS AND INFLAMMATION WITH ALPHA$_{2A}$ ADRENERGIC ANTAGONISTS, and filed simultaneously with the present application.

The present invention is also directed to methods of treating a mammal at risk for sepsis. The methods comprise treating the mammal with a milk fat globule epidermal growth factor-factor VIII (MFG-E8) sufficient to prevent or reduce a physiologic effect of the sepsis. Preferably, the MFG-E8 has an amino acid sequence at least 90% identical to SEQ ID NO:1 or SEQ ID NO:2, which are the sequences of a human MFG-E8 and mouse MFG-E8, respectively. These methods can be used with any mammal, including humans.

As in the above-described embodiments, the MFG-E8 in these embodiments can be in purified form or in combination with other therapeutic agents and/or only partially purified. The MFG-E8 can have a wild-type sequence from any mammalian species, or can comprise mutations, provided the mutations do not eliminate the protein's activity to prevent or reduce a physiologic effect of the sepsis. The MFG-E8 can also comprise peptidomimetics. Where the MFG-E8 is from MFG-E8-rich exosomes, the exosomes are preferably from the same species as the treated mammal; more preferably, the exosomes are from the same individual.

The methods of the present invention prevent or reduce physiologic effects of sepsis, such as shock, elevation of serum TNF-α levels, elevation of serum IL-6 levels, and physiological effects of altered cytokine release (e.g., inflammation). To evaluate the prevention or reduction of physiologic effects of sepsis, it is preferred that physiologic effects that are easily measured are evaluated. Examples of these effects are elevation of serum TNF-α levels, elevation of serum ALT levels, elevation of serum AST levels, elevation of serum lactate, and elevation of serum creatinine. In preferred embodiments, the measured physiological effect of the sepsis is elevation of serum TNF-α or IL-6 levels, or evaluation of thymocyte apoptosis, as in the Example.

These methods can also comprise treating the mammal with a second treatment that can reduce a physiological effect of the sepsis. Examples of such treatments include administration of adrenomedullin, adrenomedullin binding protein, activated protein C, or an α$_{2A}$-adrenergic antagonist.

In further embodiments, the invention is directed to methods of preventing or treating a physiologic effect of sepsis in a mammal. The methods comprise treating the mammal with a milk fat globule epidermal growth factor-factor VIII (MFG-E8) such that a physiologic effect of the sepsis is prevented or reduced. Preferably, the MFG-E8 has an amino acid sequence at least 90% identical to SEQ ID NO:1 or SEQ ID NO:2, which are the sequences of a human MFG-E8 and mouse MFG-E8, respectively. These methods can be used with any mammal, including humans.

As in the above-described embodiments, the MFG-E8 in these embodiments can be in purified form or in combination with other therapeutic agents and/or only partially purified. The MFG-E8 can have a wild-type sequence from any mammalian species, or can comprise mutations, provided the mutations do not eliminate the protein's activity to prevent or reduce a physiologic effect of the sepsis. The MFG-E8 can also comprise peptidomimetics. Where the MFG-E8 is from MFG-E8-rich exosomes, the exosomes are preferably from the same species as the treated mammal; more preferably, the exosomes are from the same individual.

The methods of the present invention prevent or reduce any physiologic effect of sepsis, including shock, elevation of serum TNF-α levels, elevation of serum IL-6 levels, and physiological effects of altered cytokine release (e.g., inflammation). To evaluate the prevention or reduction of physiologic effects of sepsis, it is preferred that physiologic effects that are easily measured are evaluated. Examples of these effects are elevation of serum TNF-α levels, elevation of serum ALT levels, elevation of serum AST levels, elevation of serum lactate, and elevation of serum creatinine. In preferred embodiments, the measured physiological effect of the sepsis is elevation of serum TNF-α or IL-6 levels, or evaluation of thymocyte apoptosis, as in the Example.

These methods can also comprise treating the mammal with a second treatment that can reduce a physiological effect of the sepsis. Examples of such treatments include administration of adrenomedullin, adrenomedullin binding protein, activated protein C, or an α$_{2A}$-adrenergic antagonist.

The present invention is additionally directed to the use of milk fat globule epidermal growth factor-factor VIII (MFG-E8) for the manufacture of a medicament for preventing or treating a physiologic effect of sepsis in a mammal. Preferably, the MFG-E8 has an amino acid sequence at least 90% identical to SEQ ID NO:1 or SEQ ID NO:2, which are the sequences of a human MFG-E8 and mouse MFG-E8, respectively.

In related embodiments, the invention is also directed to the use of milk fat globule epidermal growth factor-factor VIII (MFG-E8) for the treatment of a mammal having sepsis or at risk for sepsis. Preferably, the MFG-E8 has an amino acid sequence at least 90% identical to SEQ ID NO:1 or SEQ ID NO:2, which are the sequences of a human MFG-E8 and mouse MFG-E8, respectively.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

MFG-E8 Protects Against Sepsis

Apoptotic cells can harm the host in sepsis, if not cleared by phagocytes. Phagocytosis of apoptotic cells depends on "eat me" signals expressed on dying cells, such as phosphatidylserine (PS). PS can be recognized by phagocytes via its receptors. For complete engulfment of apoptotic cells, binding of PS to integrin $\alpha_v\Theta_3$, mediated by the bridging protein milk fat globule epidermal growth factor-factor VIII (MFG-E8), is needed.

We hypothesize that phagocytosis of apoptotic cells is impaired in inflammation generally, and more particularly in sepsis due to the decreased MFG-E8 and that adaptive transfer of bone marrow DC (BMDC)-derived exosomes rich in MFG-E8 is beneficial. To evaluate that hypothesis, sepsis was induced in rats by cecal ligation and puncture (CLP). The CLP model of sepsis has been used extensively as a reliable model of the pathophysiologic and immunologic alterations in human sepsis.

Figure 1:
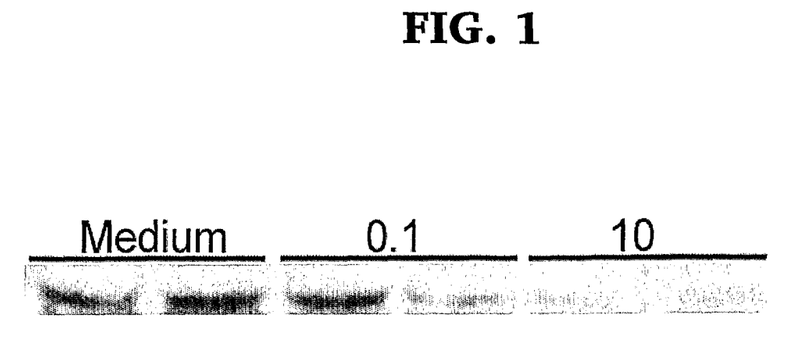
FIG. 1 shows the protein expression of MFG-E8 in RAW 264.7 macrophages (RMΦ)±LPS, where the values are LPS added, in ng/ml.
Figure 2:
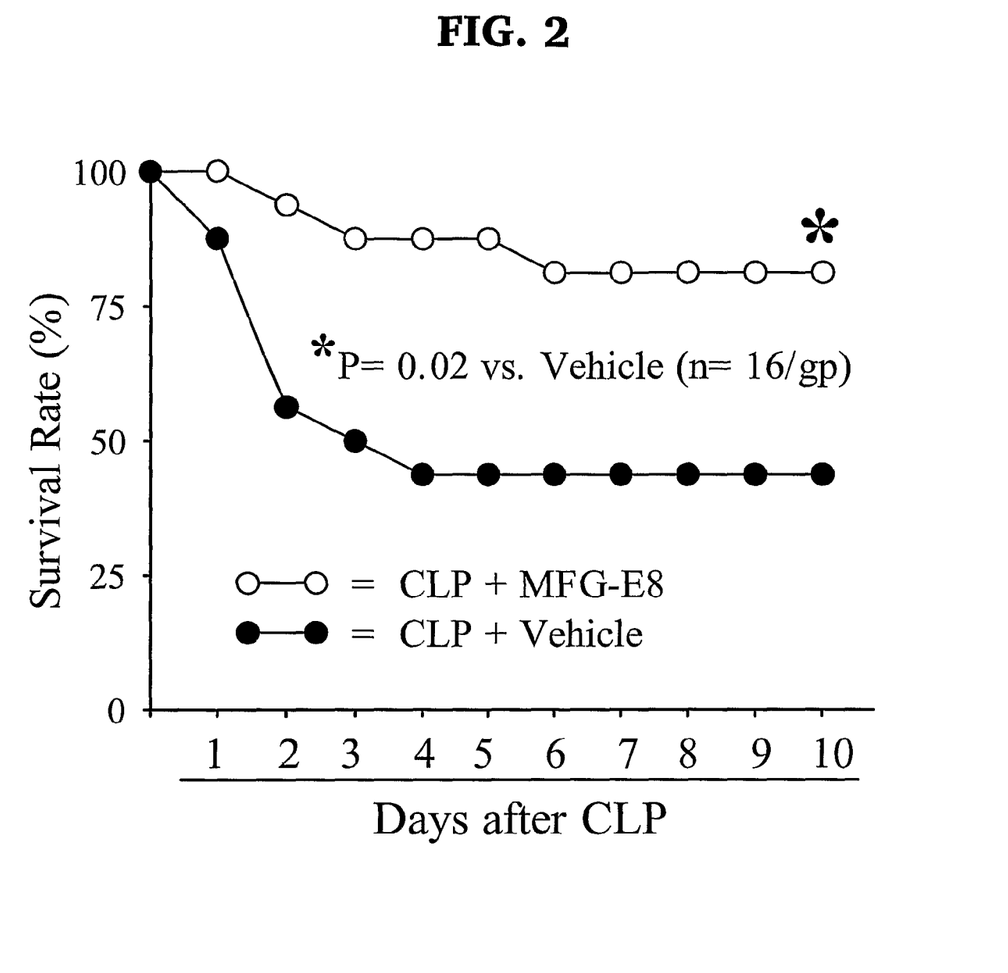
FIG. 2 is a graph of experimental results showing increased survival of rats undergoing sepsis when treated with MFG-E8.

MFG-E8 was assessed by Western blot in CLP rats and in RAW 264.7 macrophages (RMΦ) stimulated with LPS at 20 h. Exosomes (1000 μg), collected from supernatant of cultured BMDCs, were injected intravenously to septic rats at the time of CLP. Levels of cytokines TNF-α and IL-6 (pg/mL) were determined by ELISA and apoptotic thymocytes (TC-A$_o$) were detected by Annexin V. Peritoneal MΦ were cultured with exosomes (24 h) and their ability to engulf TC-$A_o$ was determined in vitro (phagocytosis index [PI]: TC-$A_o$/MΦ). Our results indicate that MFG-E8 in spleen and liver decreased by 48% and 70% respectively at 20 h after sepsis (Table 1). MFG-E8 expression also decreased after in vitro stimulation of RMΦ with LPS (FIG. 1). Injection of exosomes to CLP rats led to reduced detection of TC-$A_o$ and plasma cytokines as shown in Table 2. Moreover, peritoneal MΦ from exosome-treated rats displayed a 3.6-fold increased activity to phagocytose TC-$A_o$ (PI: 0.84±0.13 vs. 0.23±0.04 in Vehicle, P<0.05). In additional groups of rats, exosomes (250 μg each) or vehicle (PBS) were administered intravenously at the time of CLP and 5 hours after CLP. MFG-E8 significantly improved the survival rate (FIG. 2). We conclude that BMDC-derived exosomes, which are a rich source of MFG-E8, attenuate systemic inflammation and improve survival in sepsis, by enhancing clearance of apoptotic cells. The increased availability of MFG-E8, a factor indispensable for phagocytosis of apoptotic cells, is the underlying mechanism.

TABLE 1

Decrease in milk fat globule epidermal growth factor-factor VIII (MFG-E8) after induction of sepsis.

| Protein | Sham (n = 5) | CLP (n = 5) |
|---|---|---|
| Spleen | 1.08 ± 0.19 | 0.56 ± 0.06* |
| Liver | 0.67 ± 0.15 | 0.20 ± 0.04* |

MFG-E8/β-Actin;
t-test: *P < 0.05

TABLE 2

Reduced detection of apoptosis (TC-$A_o$) and plasma cytokines after exosome injection to cecal ligation and puncture (CLP) rats.

| N = 6 | Sham (%) | CLP Vehicle (%) | CLP Exosomes (%) |
|---|---|---|---|
| TC-$A_o$ (%) | 4.7 ± 0.07 | 12.2 ± 3.1* | 8.2 ± 0.3# |
| TNF-α (pg/ml) | 4.9 ± 1.2 | 30.4 ± 8.6* | 15.7 ± 2.1# |
| IL-6 (pg/ml) | 90.9 ± 15.1 | 545.7 ± 119.5* | 319.0 ± 28.5* |

Values are mean ± SEM;
ANOVA: *P < 0.05 vs. Sham;
P < 0.05 vs. Vehicle

Example 2

Further MFG-E8 Studies

Sepsis Reduces MFG-E8 Expression.

Figure 3:
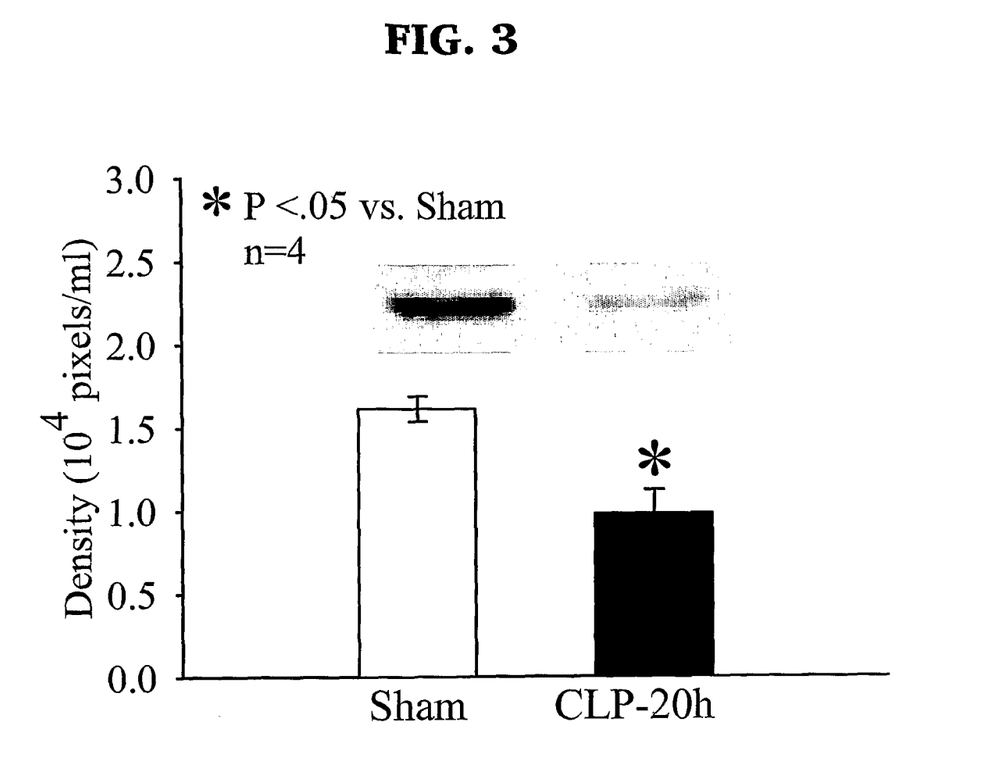
FIG. 3 is a graph of experimental results showing that plasma MFG-E8 levels decrease 20 hours after CLP.

Rat MFG-E8 protein expression was determined by Western blot analysis using specific antibodies (goat anti-rat MFG-E8 IgG clone G-17, from Santa Cruz). Plasma MFG-E8 decreased significantly 20 h after CLP (FIG. 3).

Figure 4:
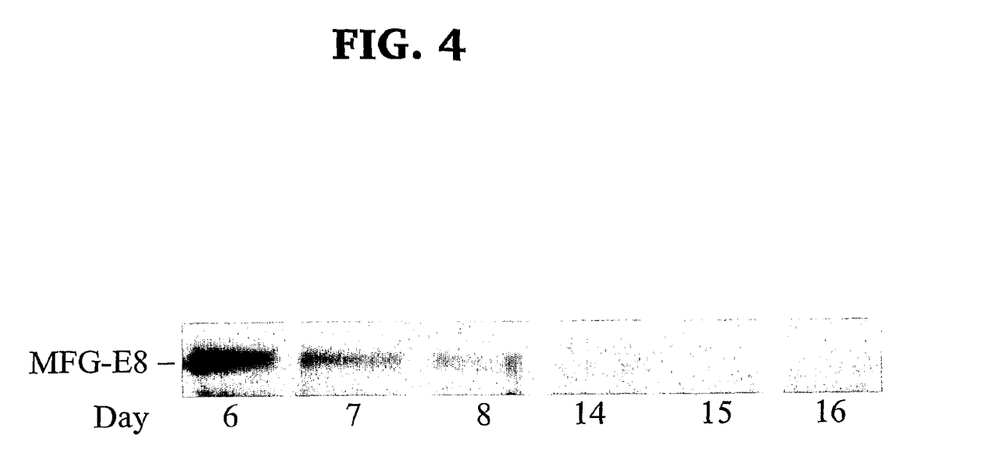
FIG. 4 is photographs of western blots showing that MFG-E8 is only expressed in immature dendritic cells (6-8 day culture).

Expression of MFP-E8 was evaluated in BMDCs over time. From days 4-16, BMDCs were cultured with exosome-free FBS. Culture medium was collected and gradually centrifuged to remove cells and bigger particles and vesicles, and then ultracentrifuged at 100,000×g to obtain exosomes. The collected pellet was washed and reconstituted with PBS, the amount of protein was assessed and the emulsion was adjusted to a concentration of 1 mg/ml in PBS. The existence of MFG-E8 in the exosome fraction was verified by Western blot with a maximal content of this protein on day 6 of BMDC culture (FIG. 4). Thus, MFG-E8 is only expressed in immature dendritic cells. Exosomes collected on days 6-8 were used as MFG-E8-containing (MFG-E8+) exosomes and those collected on days 14-16 were used as non-MFG-E8-containing exosomes.

Figure 5:
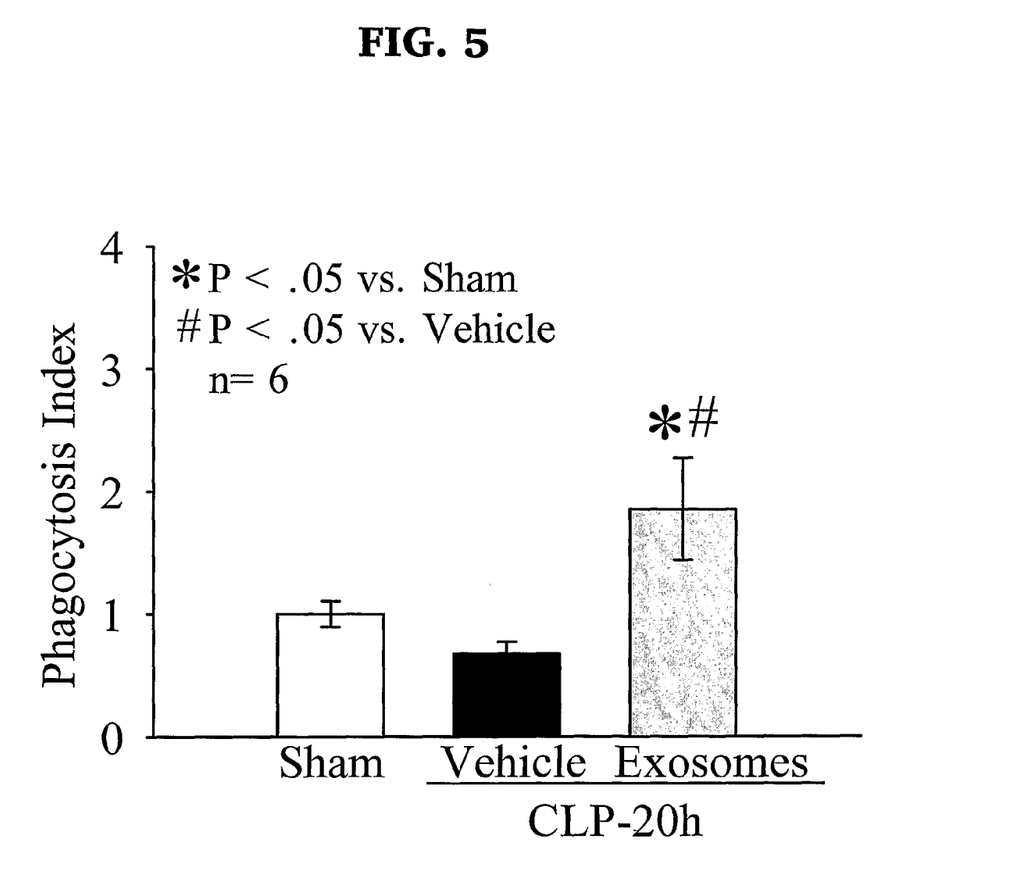
FIG. 5 is a graph of experimental results showing that peritoneal MΦ isolated from septic rats treated with MFG-E8+ exosomes increases the phagocytosis index of those cells.

The effect of MFG-E8 on apoptosis was further evaluated. FIG. 5 shows that the phagocytosis index (a ratio of apoptotic cells/MΦ; normalized to 1.0 in sham-operated animals) in vehicle-treated septic animals decreased by 32.6% as compared to sham-operated animals (P=0.021 by Student's t test for the two groups only, but one-way ANOVA, a more appropriate test, did not show a statistical difference between sham and vehicle-treated CLP rats). However, MFG-E8+ exosomes increased the phagocytosis index by 174.7% and 85.2%, as compared to vehicle-treated CLP and sham animals, respectively (P<0.05 by ANOVA). Thus, administration of MFG-E8+ exosomes reduces apoptosis, downregulates cytokines, and improves phagocytosis in sepsis. In contrast, non-MFG-E8-containing exosomes did not demonstrate any anti-apoptotic, anti-inflammatory, and phagocytotic properties (data not shown), indicating MFG-E8 is responsible for the observed effects.

Figure 6:
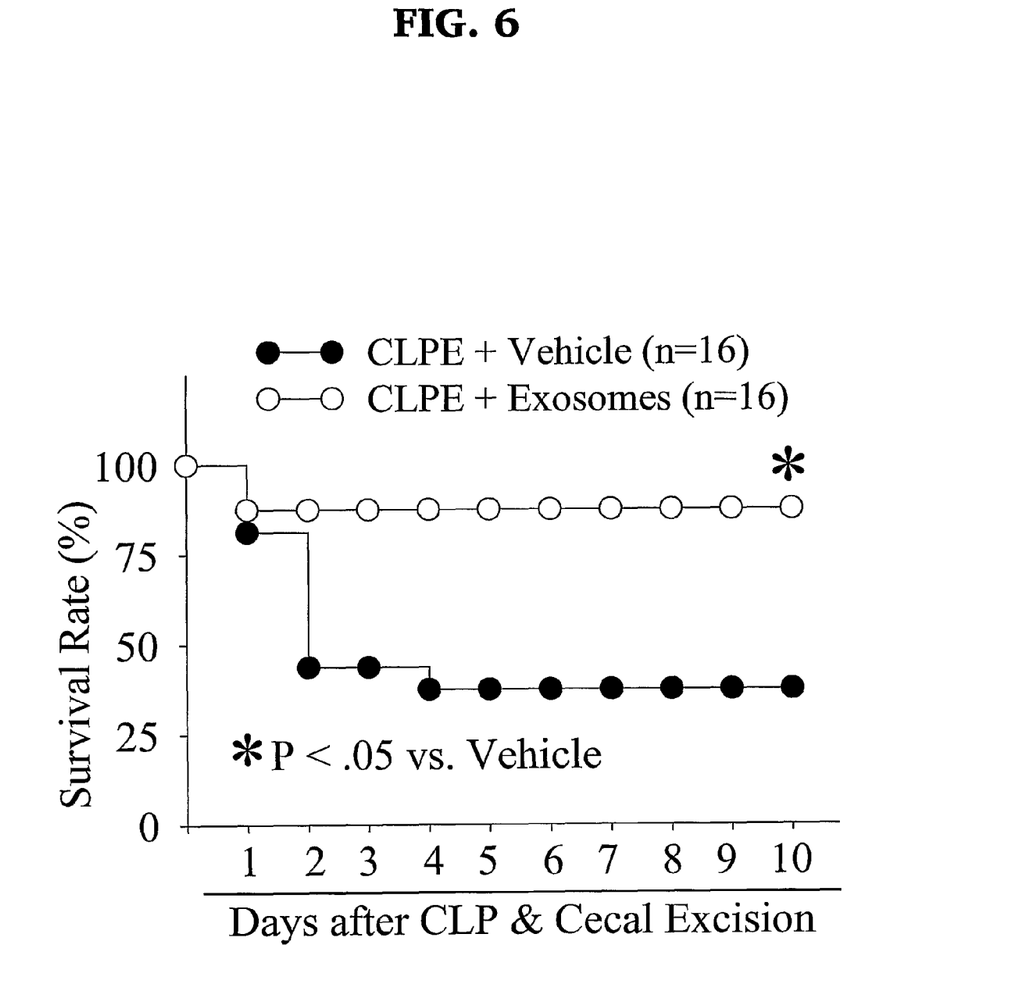
FIG. 6 is a graph of experimental results showing that administration of MFG-E8+ exosomes to rats 5 and 20 hours after CLP (i.e., post-treatment) increases survival.

When MFG-E8+ exosomes were given intravenously at 5 and 20 h after CLP (i.e., post-treatment), survival was markedly improved (FIG. 6). However, the survival advantage was not observed when non-MFG-E8-containing exosomes were given. Non-MFG-E8-containing exosome-treated septic rats had even a slightly worse outcome as compared to vehicle-treated septic animals (data not shown).

The Specificity of MFG-E8 on Exosomes is Confirmed by the Blocking Antibodies.

Figure 7:
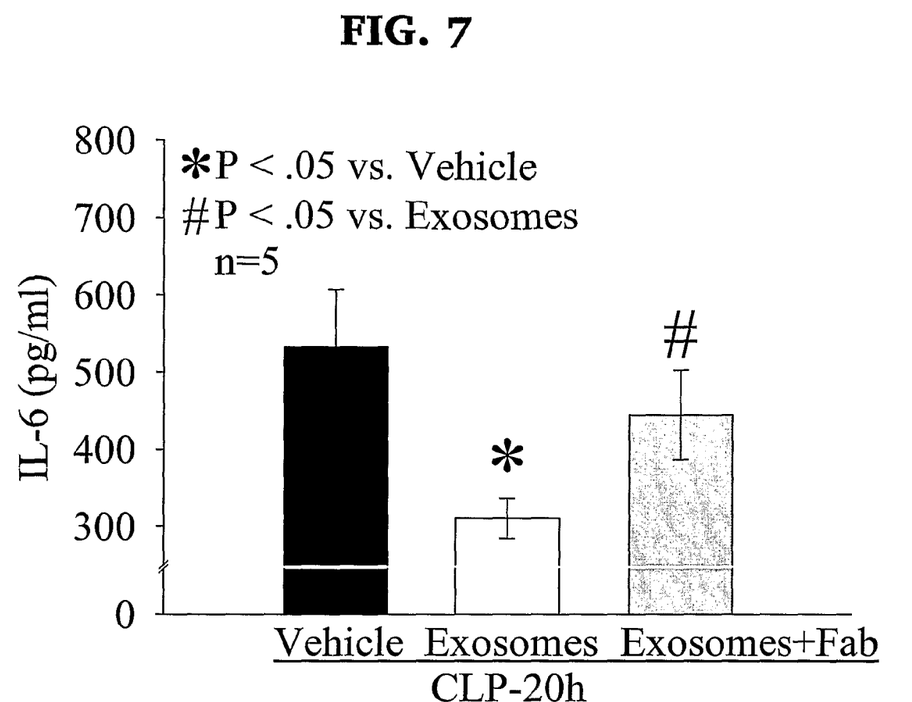
FIG. 7 is a graph of experimental results showing that anti-MFG-E8 antibodies prevents downregulation of IL-6 induced by MFG-E8.

BMDC-derived exosomes may contain several other proteins that could influence our findings. To further confirm that MFG-E8 is indeed the molecule responsible for the above beneficial effects in sepsis, blocking antibodies were used to inhibit MFG-E8 on exosomes prior to injection into septic rats. In order to avoid interference with phagocytosis by binding to Fcγ-receptors on phagocytes, Fab-fragments were used instead of complete antibodies to block MFG-E8. The result indicates that MFG-E8+ exosome-mediated decrease of apoptotic thymocytes and increase in phagocytosis in septic rats can be completely reversed by inhibiting MFG-E8 prior to the injection of exosomes. Even in the absence of sepsis (i.e., sham rats), the Fab-fragment of the anti-MFG-E8 antibodies induced a surge in apoptotic thymocytes (data not shown). In addition, MΦ from non-septic rats receiving anti-MFG-E8 Fab decreased their ability to engulf apoptotic cells to almost undetectable levels (phagocytosis index: 0.067±0.007 vs. 1.000±0.31 in control rats, n=−5). Furthermore, the inhibitory effect of MFG-E8+ exosomes on plasma IL-6 levels in sepsis was prevented with the anti-MFG-E8 antibodies (Fab) (FIG. 7). These findings further confirm the specificity of MFG-E8 in BMDC-derived exosomes (collected day 6-8).

Evaluation of Recombinant MFG-E8 (rMFG-E8).

Figure 8:
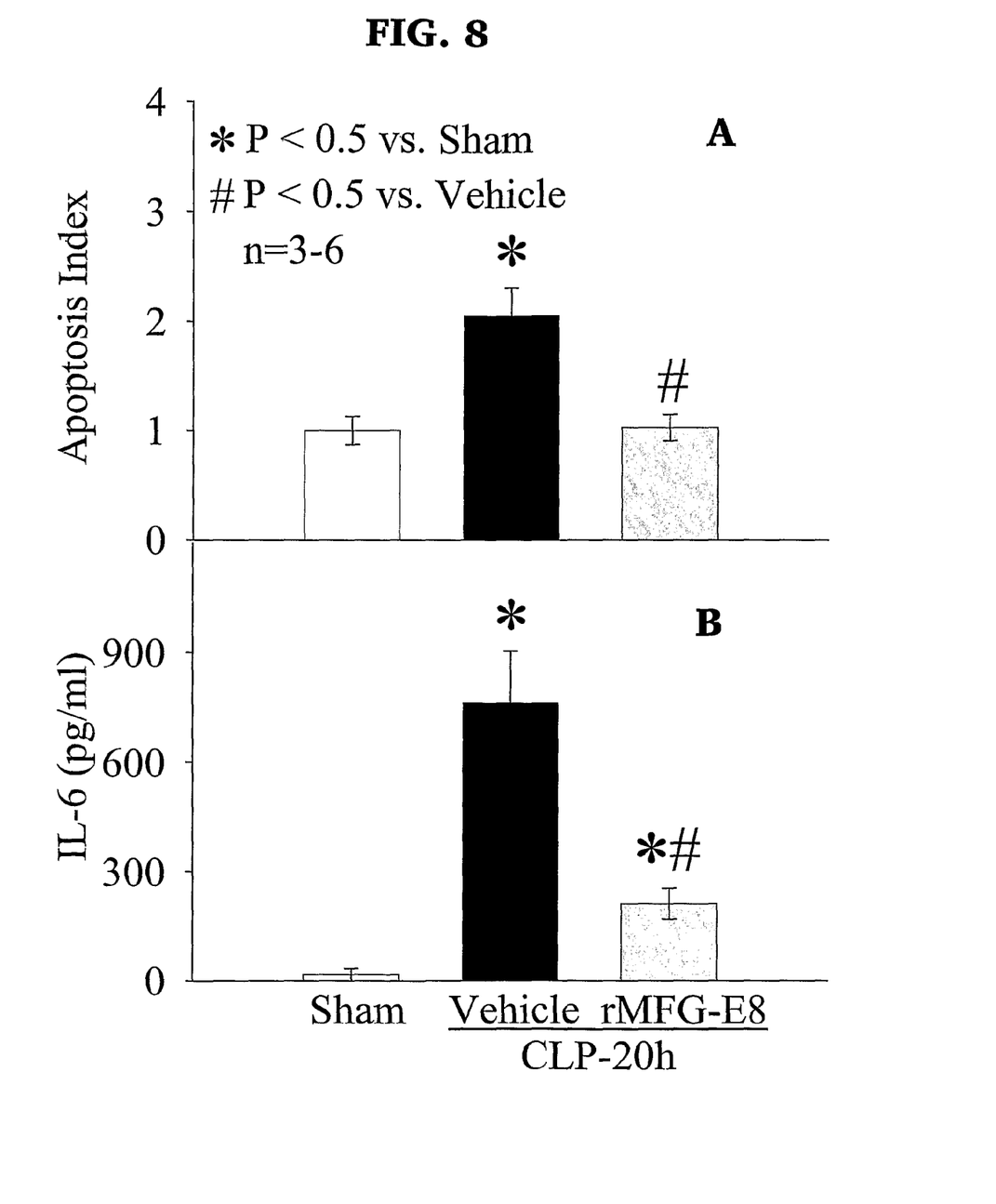
FIG. 8 is a graph of experimental results showing that rMFG-E8 increases the phagocytosis index (Panel A) and attenuates IL-6 levels (Panel B) after CLP.
Figure 9:
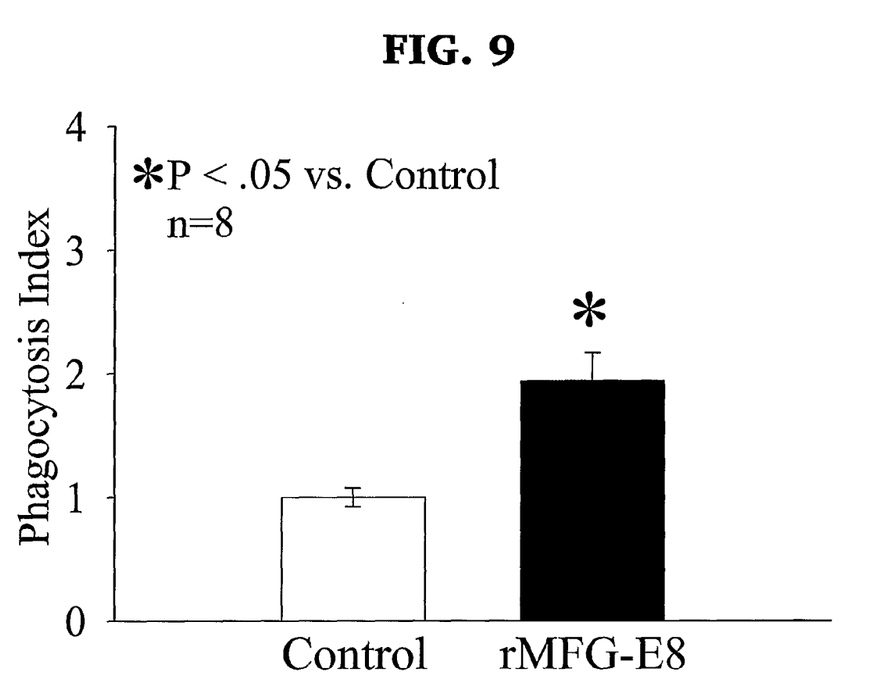
FIG. 9 is a graph of experimental results showing that rMFG-E8 increases peritoneal MΦ phagocytosis index in vitro.
Figure 10:
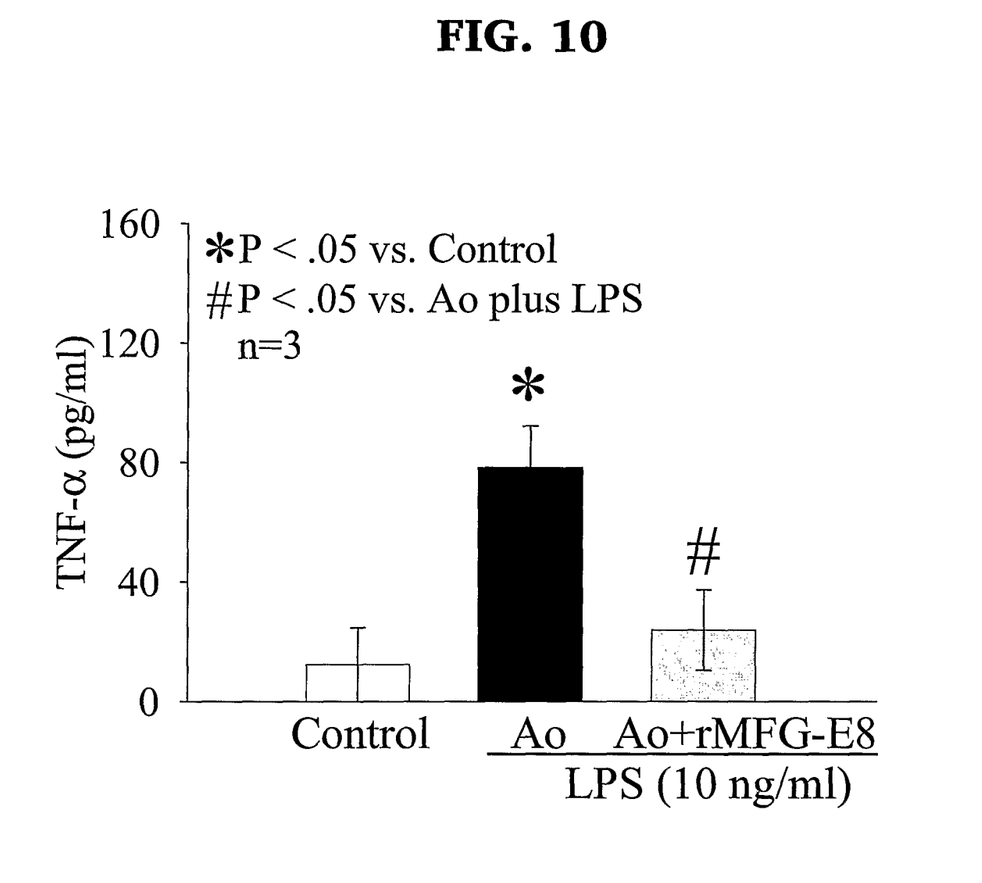
FIG. 10 is a graph of experimental results showing that rMFG-E8 decreases peritoneal MΦ TNF-α release after 3 h incubation in low-dose LPS and apoptotic thymocytes.

Due to the glycosylation nature of MFG-E8, commercial rMFG-E8 has not been developed until very recently. The results presented below indicate that rMFG-E8 is as effective as BMDC-derived MFG-E8+ exosomes. The mouse rMFG-E8 (R & D Systems, Minneapolis, Minn.) used in our study is >95% purity with a molecular weight of 67 kDa (identical to the naturally occurring mouse MFG-E8), and of at least 95% homology to rat MFG-E8. Moreover, our initial test indicates that mouse rMFG-E8 is highly effective in the rat. Intravenous administration of rMFG-E8 at a dose of 20 μg/kg BW significantly attenuated the increase in thymocyte apoptosis (FIG. 8A) and elevation of plasma IL-6 levels (FIG. 8B) 20 h after CLP. Since UL-6 has been used as a measure of not only inflammation but also tissue injury, rMFG-E8-mediated decrease in plasma IL-6 may reflect its protection on tissue injury. Under in vitro conditions, rMFG-E8 (10 μg/ml) markedly increased peritoneal MΦ's phagocytosis index following pre-incubation for 1 h (FIG. 9). In addition, rMFG-E8 (10

μg/ml) significantly decreased TNF-α release from peritoneal MΦ after 3 h incubation in the presence of low-dose LPS (10 ng/ml) and apoptotic thymocytes (FIG. 10). Thus, rMFG-E8 effectively increases apoptotic cell clearance and attenuates inflammation.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of reducing thymocyte apoptosis in sepsis in a human, the method comprising administering to the human at least 20 μg/kg body weight (BW) an amount of a milk fat globule epidermal growth factor-factor VIII (MFG-E8), wherein the MFG-E8 has an amino acid sequence at least 99% identical to SEQ ID NO:1, and wherein the MFG-E8 is administered by intravenous administration.

2. The method of claim 1, wherein the human is administered MFG-E8-rich exosomes derived from mammalian cells.

3. The method of claim 1, wherein the MFG-E8 is recombinant MFG-E8.

4. The method of claim 1, wherein the MFG-E8 has an amino acid sequence as set forth in SEQ ID NO:1.

5. The method of claim 1, wherein the sepsis is surgical sepsis.

* * * * *

SEQUENCE LISTING

```
<160> NUMBER OF SEQ ID NOS: 2

<210> SEQ ID NO 1
<211> LENGTH: 387
<212> TYPE: PRT
<213> ORGANISM: Homo sapiens

<400> SEQUENCE: 1

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
    290                 295                 300
```

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
370                 375                 380

Leu Gly Cys
385

<210> SEQ ID NO 2
<211> LENGTH: 463
<212> TYPE: PRT
<213> ORGANISM: Mus musculus

<400> SEQUENCE: 2

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
145                 150                 155                 160

Asp Ser Gln Ile Ser Ala Ser Tyr Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp His Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255

Asp Lys Glu Phe Leu Gly Asn Leu Asp Asn Asn Ser Leu Lys Val Asn
            260                 265                 270

Met Phe Asn Pro Thr Leu Glu Ala Gln Tyr Ile Arg Leu Tyr Pro Val

```
                    275                 280                 285
Ser Cys His Arg Gly Cys Thr Leu Arg Phe Glu Leu Leu Gly Cys Glu
    290                 295                 300

Leu His Gly Cys Leu Glu Pro Leu Gly Leu Lys Asn Asn Thr Ile Pro
305                 310                 315                 320

Asp Ser Gln Met Ser Ala Ser Ser Tyr Lys Thr Trp Asn Leu Arg
                325                 330                 335

Ala Phe Gly Trp Tyr Pro His Leu Gly Arg Leu Asp Asn Gln Gly Lys
            340                 345                 350

Ile Asn Ala Trp Thr Ala Gln Ser Asn Ser Ala Lys Glu Trp Leu Gln
            355                 360                 365

Val Asp Leu Gly Thr Gln Arg Gln Val Thr Gly Ile Ile Thr Gln Gly
    370                 375                 380

Ala Arg Asp Phe Gly His Ile Gln Tyr Val Glu Ser Tyr Lys Val Ala
385                 390                 395                 400

His Ser Asp Asp Gly Val Gln Trp Thr Val Tyr Glu Glu Gln Gly Ser
                405                 410                 415

Ser Lys Val Phe Gln Gly Asn Leu Asp Asn Asn Ser His Lys Lys Asn
                420                 425                 430

Ile Phe Glu Lys Pro Phe Met Ala Arg Tyr Val Arg Val Leu Pro Val
            435                 440                 445

Ser Trp His Asn Arg Ile Thr Leu Arg Leu Glu Leu Leu Gly Cys
    450                 455                 460
```